United States Patent
Rasmusson et al.

(10) Patent No.: US 11,363,974 B2
(45) Date of Patent: Jun. 21, 2022

(54) METHOD AND DEVICE FOR BLOOD GLUCOSE LEVEL MONITORING

(71) Applicant: Sony Mobile Communications Inc., Tokyo (JP)

(72) Inventors: Jim Rasmusson, Lund (SE); Peter C Karlsson, Lund (SE); Magnus Svensson, Lomma (SE); Claes Nilsson, Lund (SE); Jimmy Eklund, Lund (SE)

(73) Assignee: Sony Group Corporation, Tokyo (JP)

(*) Notice: Subject to any disclaimer, the term of this patent is extended or adjusted under 35 U.S.C. 154(b) by 251 days.

(21) Appl. No.: 16/426,913

(22) Filed: May 30, 2019

(65) Prior Publication Data
US 2019/0365301 A1 Dec. 5, 2019

(30) Foreign Application Priority Data
May 30, 2018 (SE) .................. 1850652-7

(51) Int. Cl.
*A61B 5/145* (2006.01)
*A61B 5/00* (2006.01)

(52) U.S. Cl.
CPC ........ *A61B 5/14532* (2013.01); *A61B 5/4803* (2013.01); *A61B 5/681* (2013.01);
(Continued)

(58) Field of Classification Search
CPC ..... A61B 5/14532; A61B 5/4803; A61B 5/72; A61B 5/7221; A61B 5/7275;
(Continued)

(56) References Cited

U.S. PATENT DOCUMENTS 7,398,213 B1  7/2008 Levanon et al.
7,925,508 B1  4/2011 Michaelis
(Continued)

FOREIGN PATENT DOCUMENTS

DE  10 2015 218948 A1  3/2017
DE  102015218948 A1 *  3/2017
(Continued)

OTHER PUBLICATIONS

Machine translation of Saeltzer et al. (DE 102015218948 A1) (Year: 2022).*
(Continued)

*Primary Examiner* — Eric F Winakur
*Assistant Examiner* — Alice Ling Zou
(74) *Attorney, Agent, or Firm* — Renner, Otto, Boisselle & Sklar, LLP

(57) ABSTRACT

A method for monitoring a blood glucose level of an individual comprises the steps of receiving (S1) a first glucose value, which has been measured in a body fluid of the individual other than the individual's blood, the first glucose value representing the blood glucose level of the individual with a first delay; receiving (S6) speech of the individual; analyzing (S7) the individual's speech; and determining (S8) a supplementary glucose value, which represents the blood glucose level of the individual with a shorter delay than the first delay; wherein the determination of the supplementary glucose value is based on the analyzing of the individual's speech.

18 Claims, 4 Drawing Sheets

(52) U.S. Cl.
CPC .............. *A61B 5/72* (2013.01); *A61B 5/6822* (2013.01); *A61B 5/6824* (2013.01); *A61B 5/6831* (2013.01); *A61B 5/7282* (2013.01)

(58) Field of Classification Search
CPC ... A61B 5/7271; A61B 5/7282; A61B 5/1455; A61B 5/1459; A61B 5/1468–1473; A61B 5/1477; A61B 5/1486–14865
See application file for complete search history.

(56) References Cited

U.S. PATENT DOCUMENTS

| | | | |
|---|---|---|---|
| 2003/0125612 A1 | 7/2003 | Fox et al. | |
| 2006/0142651 A1* | 6/2006 | Brister | A61B 5/14865 600/347 |
| 2010/0234710 A1* | 9/2010 | Budiman | A61B 5/14865 600/365 |
| 2011/0190701 A1 | 8/2011 | Remde et al. | |
| 2011/0313774 A1 | 12/2011 | Ji et al. | |
| 2014/0278123 A1 | 9/2014 | Prodhom et al. | |
| 2015/0164389 A1* | 6/2015 | Varsavsky | A61B 5/7278 600/316 |

FOREIGN PATENT DOCUMENTS

| | | | |
|---|---|---|---|
| RU | 2 506 893 | 2/2014 | |
| WO | 2014/049438 A2 | 4/2014 | |
| WO | 2014/072823 A2 | 5/2014 | |
| WO | WO-2016151479 A1 * | 9/2016 | ............. G16H 40/67 |
| WO | 2018/002107 A1 | 1/2018 | |

OTHER PUBLICATIONS

European Search Report for corresponding European Patent Application No. 19 17 1632 dated Oct. 16, 2019.

European Search Opinion for corresponding European Patent Application No. 19 171 632.3.

Audrey Farley, *Speech Recognition Software Improves Bolus Calculation, Another Study Suggest*, http://insulinnation.com/treatment/polish-study-offers-further-evidence-that-speech-recognition-software-improves-bolus-calculation/, Jan. 17, 2018.

fredkon@yandex.ru, *In speech nothing, exclusive mathematics*, http://fred.ucoz.ru/.

Office Action for counterpart Swedish Patent Application No. 1850652-7 dated Dec. 6, 2018.

* cited by examiner

METHOD AND DEVICE FOR BLOOD GLUCOSE LEVEL MONITORING

TECHNICAL FIELD

The invention relates to a method and a device for monitoring a blood glucose level of an individual.

BACKGROUND ART

According to the World Health Organization's Global Report on Diabetes almost half a billion people suffer from diabetes. It is an rapidly increasing disease which may lead to severe complications. In 2012 alone, diabetes caused 1.5 million deaths.

Insulin is a hormone that regulates the blood glucose level in the body. Diabetes occurs either when the amount of insulin produced by the pancreas is insufficient or when the insulin is not sufficiently effective. To avoid short-term and long-term complications, a diabetic needs to monitor the glucose level in her blood so that it neither drops too low, nor rises too high.

Traditionally, a diabetic has determined her blood glucose level by taking a sample of blood from her finger and analyzing it in an instrument that determines the blood glucose level, typically by optical or chemical methods.

In more recent years, systems for continuous measuring of blood glucose levels have gained widespread use. A continuous glucose monitor (CGM) uses a small sensor placed under the skin of the diabetic to measure glucose values which are wirelessly transmitted to a receiver, e.g. a mobile phone or a dedicated device, carried by the diabetic. Measured glucose values and related information are presented on a display of the receiver.

A limitation of the CGM system is that glucose levels are measured in the interstitial fluid rather than in the blood. As it takes time for glucose to travel from the blood into the interstitial fluid, there is an inherent delay between the current blood glucose level and the level measured by the CGM. This delay may amount to as much as 20 minutes, which is a very long time if the blood glucose level unexpectedly starts to move in the wrong direction. Also when the blood glucose level behaves as expected, the delay may cause concerns and even trigger inappropriate actions. Consider for example the situation where a diabetic has a low blood glucose level and eats sugar to raise the glucose level. It will then take some time before the CGM can confirm that the glucose level is on its way up. As a result the diabetic may be worried and eat more sugar to compensate for the CGM's lack of indication of a raised glucose level, ending up with an overcompensation of the initially low blood glucose level.

Some CGM systems include a predictor function, which gives the diabetic an earlier indication of the blood glucose level than what the actual CGM value gives. However, the predictor function only uses CGM values for the prediction, and if something unexpected occurs, the prediction may fail.

If a diabetic suspects that her blood glucose level deviates from what the CGM system indicates, she may check the blood glucose level by a blood sample, which shows the blood glucose value in real time. However, in some situations an instrument to analyze the blood sample may not be available. Also, some diabetics may experience discomfort when taking blood samples.

SUMMARY

It is an objective of the invention to at least partly overcome one or more limitations of the prior art.

This objective as well as further objectives that may appear from the description below, are at least partly achieved by a method and a device according to the independent claims, embodiments thereof being defined by the dependent claims.

According to one aspect of the invention, a method for monitoring a blood glucose level of an individual comprises the steps of receiving a first glucose value, which has been measured in a body fluid of the individual other than the individual's blood, the first glucose value representing the blood glucose level of the individual with a first delay; receiving speech of the individual; analyzing the individual's speech; and determining a supplementary glucose value, which represents the blood glucose level of the individual with a shorter delay than the first delay; wherein the determination of the supplementary glucose value is based on the analyzing of the individual's speech.

According to another aspect of the invention, a device for monitoring a blood glucose level of an individual, comprises a first interface for receiving a first glucose value, which has been measured in a body fluid of the individual other than the individual's blood, the first glucose value representing the blood glucose level of the individual with a first delay, a second interface for receiving speech from the individual, and control circuitry configured to analyze the individual's speech and to determine a supplementary glucose value, which represents the blood glucose level of the individual with a shorter delay than the first delay; wherein the determination of the supplementary glucose value is based on the analyzing of the individual's speech.

When the glucose level of an individual moves out of an acceptable range, i.e. drops too low or rises too high, the speech of the individual will be almost immediately affected. By analyzing speech of the individual, it will be possible to determine a supplementary glucose value, which represents the blood glucose value with no or little delay and which thus can serve as a true predictor to the first glucose value which represents the blood glucose level with some delay.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

DETAILED DESCRIPTION OF EXAMPLE EMBODIMENTS

The following disclosure relates to blood glucose monitoring by means of a first glucose value which has been measured in a body fluid of an individual other than the individual's blood, the first glucose value representing the blood glucose level of the individual with a first delay, and a supplementary glucose value which represents the blood glucose level of the individual with a shorter delay than the first delay, wherein the supplementary glucose value is based on an analysis of the individual's speech.

As has been explained above, the delay or lag between the actual glucose level in the blood on the one hand and the glucose level measured in another body fluid, such as the interstitial fluid, on the other hand may give rise to concern and even potentially dangerous situations. By supplementing the glucose value measured in the non-blood body fluid with a glucose value or glucose indication determined by an analysis of the individual's speech, which is immediately or with very little delay affected by a deviation of the blood glucose value from the normal, one and more of the problems associated with the delayed measurement can be alleviated as will be further explained in the following.

Figure 1:
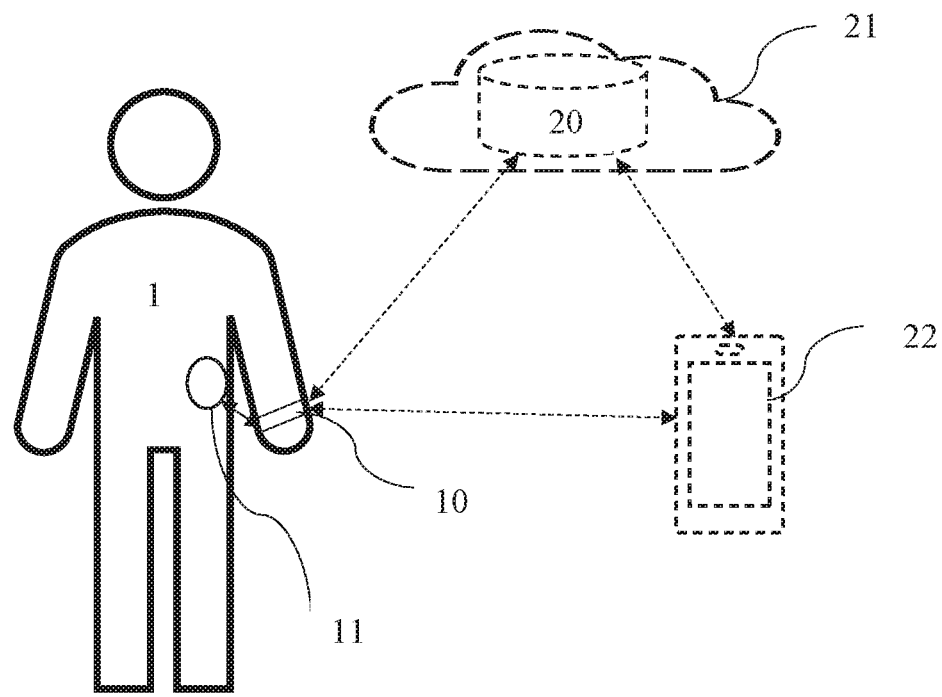
FIG. 1 schematically illustrates embodiments of a system for monitoring a blood glucose level.

FIG. 1 illustrates, with solid lines, a first embodiment of a blood glucose monitoring system, which comprises a sensor 11 for measuring a first glucose value in a body fluid other than blood, and a device 10 for blood glucose monitoring (in the following also called a glucose monitor). The sensor 11 is placed on an individual 1, who could be a diabetic or a person who needs to have his or her blood glucose level monitored for another reason (in the following only referred to as a diabetic). The glucose monitor 10 may be a dedicated device which is primarily used for blood glucose monitoring or it can be a general device which is primarily used for other purposes, but which has been adapted to also provide the blood glucose monitoring function. Examples of general devices include smartphones, PDAs, laptops, smartwatches and other digital devices that are often carried by people in everyday life. The adaptation may comprise installing an application or other software for blood glucose monitoring in the general device. The device 10 monitors the individual's blood glucose level based on at least one first glucose value from the sensor 11 and at least one supplementary glucose value determined from an analysis of speech recorded from the individual.

The glucose sensor 11 may be any kind of sensor which is suitable for measuring a glucose value in a body fluid other than blood. A common type of commercially available sensor is fastened in the skin and includes a measurement head in the form of a soft needle which is stuck into the body tissue. It measures the glucose level in the interstitial body fluid. Such a sensor is also commonly provided with a transmitter for wireless transfer of the measured glucose values to a receiver. The glucose level is continuously measured and the sensor is therefore usually called a CGM sensor where CGM stands for Continuous Glucose Measurement or Continuous Glucose Monitoring. The measured glucose values are transferred to the glucose monitor 10 at a predetermined frequency. Another sensor measures the glucose level in the same way, but does not transfer the glucose values automatically to a receiver, but the sensor needs to be actively read by the receiver. Still other types of sensors may have a different construction and/or measure the glucose level in another body fluid, like in the tears or in the exhalation air.

Figure 2:
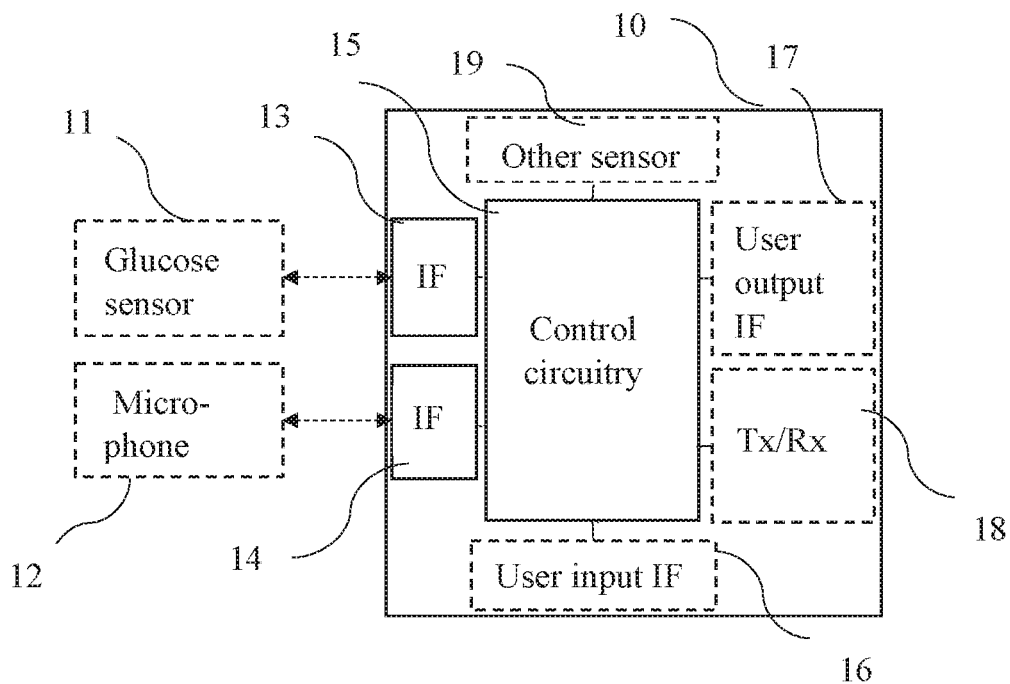
FIG. 2 is a block diagram and schematically illustrates an embodiment of a system for monitoring a blood glucose level more in detail.

FIG. 2 illustrates an embodiment of the glucose monitor 10 more in detail. It has a first input interface 13 for receiving glucose values from the glucose sensor 11, a second input or interface 14 for receiving speech from the individual and control circuitry 15 for analyzing speech and determining a supplementary glucose value.

The first interface 13 is an interface that is configured for receiving signals from the glucose sensor 11. The signals may be received by wire or wirelessly, e.g. via Bluetooth (trademark), NFC (Near Field Communication) or other kinds of radio communication. They could also be received via Body Coupled Communication through the body of the individual.

The second interface 14 is an interface that is configured to receive an audio signal from a microphone 12 which may be built into the device 10 or be an external microphone.

The control circuitry 15 may be any hardware, software, or combination thereof that is capable of performing the functions described herein. In some embodiments the controls circuitry comprises a processor and memory. The processor may be a generic processor, e.g. a microprocessor, microcontroller, CPU, DSP (digital signal processor), GPU (graphics processing unit), etc., or a specialized processor, such as an ASIC (application specific integrated circuit) or an FPGA (field programmable gate array), or any combination thereof. The memory may include volatile and/or non-volatile memory such as read only memory (ROM), random access memory (RAM) or flash memory. It may store instructions which controls the processor to perform the steps of the method and data used for performing the method. Speech from the individual may also be recorded in the memory.

The control circuitry 15 receives glucose values from the first interface 13 and speech from the second interface 14 and these input values are processed by the control circuitry 15 as will be further explained below.

In some embodiments, the glucose monitor 10 has a user input interface 16, which may include one or more hard or soft buttons, keys, controls, touch sensitive screens or any other commonly known input means. It may be used by the diabetic to provide different instructions or input to the glucose monitor 10, such as an instruction to initiate recording and analysis of speech to determine a supplementary glucose value, an instruction to turn on the microphone 12, input regarding intake of food or drinks, or input of other information that could be relevant for the evaluation and/or monitoring of the glucose value.

In some embodiments, the glucose monitor 10 has a user output interface 17, which may include a display, a speaker, one or more LEDs or other commonly known output means that can provide indications to the user. Results from the analyzing and processing performed by the control circuitry 15 may be output on the user output interface 17. Examples of such results include current and previous glucose values from the glucose sensor 11 and from the speech analysis, prompts to the diabetic to take different actions, such as initiating or triggering recording and analysis of speech to determine a supplementary glucose value, eating sugar, injecting insulin, taking a blood sample or replacing the glucose sensor 11.

In some embodiments, the control circuitry 15 uses the first and/or second interfaces 13 and 14 to provide signals to the glucose sensor 11 and/or the microphone 12. Such signals may include calibration signals to the glucose sensor 11 and a turn on/off signal to the microphone 12. Alternatively, control circuitry 15 may include separate interfaces for providing signals to the glucose sensor 11 and/or the microphone 12.

In some embodiments glucose monitor 10 includes one or more transmitters and/or receivers 18 for communication with other local or remote units. Communication may occur over computer networks and in some embodiments the glucose monitor 10 is enabled for connection to a computer network.

In some embodiments, the glucose monitor 10 includes or is connected to one or more other sensors 19 that may provide information that can be relevant for the evaluation of the blood glucose level and/or for the triggering of the determination of the supplementary glucose value. Examples of such sensors include a pulse sensor, a temperature sensor, a sleep sensor, a GPS, and an accelerometer.

As has been mentioned above, glucose monitor 10 may be a dedicated device or a general device that has been adapted for the purpose. In some embodiments, the device 10 is a wearable configured to be carried by the individual. It may for instance be a part of a clothing or accessory worn by the diabetic and it may be built into or be designed as a bracelet (as schematically illustrated in FIG. 1), a wristband, a watch, a ring, a necklace or the like.

In some embodiments, the glucose monitor 10 is a portable device carried by the diabetic or another user of the system.

Glucose values may be automatically transferred from the sensor 11 or on demand. In some embodiments the glucose monitor 10 may have to scan or otherwise be placed close to the sensor 11 to transfer glucose values from the sensor 11 to the monitor 10.

In some embodiments, the glucose monitor 10 is a remote device to which glucose values from the glucose sensor 11 and speech recorded by the microphone 12 are transmitted, optionally through an intermediary unit (not shown). The remote device may be embodied as a virtual computing device on a computer network, like the Internet, i.e. through cloud computing.

Returning to FIG. 1, which by broken lines illustrates further units or parts that may be included in some embodiments of a system for blood glucose monitoring. More particularly, the system may comprise a server 20 or a backend system implemented in the cloud 21 and/or one or more user communication devices 22, e.g. a smartphone, a smartwatch, a laptop, or the like, carried by the diabetic and/or any other person who also is a user of the system, like a relative to the diabetic or health care personnel.

In some embodiments, the glucose monitor 10 forwards first glucose values measured by the glucose sensor 11 and/or supplementary glucose values as determined by the control circuitry 15 to the server 20, which makes further calculations and assessments relating to the blood glucose level, such as short-term and long-term trends, averaging, comparisons to reference levels, and the like. Results of such further calculations and assessments may be made available for presentation on the glucose monitor 10 and/or the user communication device(s) 22.

In some embodiments, the glucose monitor 10 forwards glucose values measured by the sensor and/or supplementary glucose values as determined by the control circuitry 15 only to the one or more user communication devices 22, where further calculations, assessments and/or presentation is performed. In such case there may be no cloud connection.

In other embodiments, some information is transmitted to the cloud and other information directly to the one or more user communication devices 22.

In some other embodiments, the glucose monitor 10 is embodied in the server or backend system 20 or in a user communication device 22. In such case, the device worn by the diabetic in FIG. 1 may be replaced by a receiver/transmitter that receives glucose values from the glucose sensor 11 and speech from an external or built-in microphone 12 and that forwards this data to the glucose monitor 10 embodied in the cloud or in the user communication device 22. The output of the control circuitry 15 may in such case be made available on a user output interface on the receiver/transmitter or on the user communication device 22.

The glucose monitor 10 may also be connected to an insulin pump (not shown) and configured to transfer control signals to the insulin pump based on the results of the blood glucose monitoring.

Figure 3:
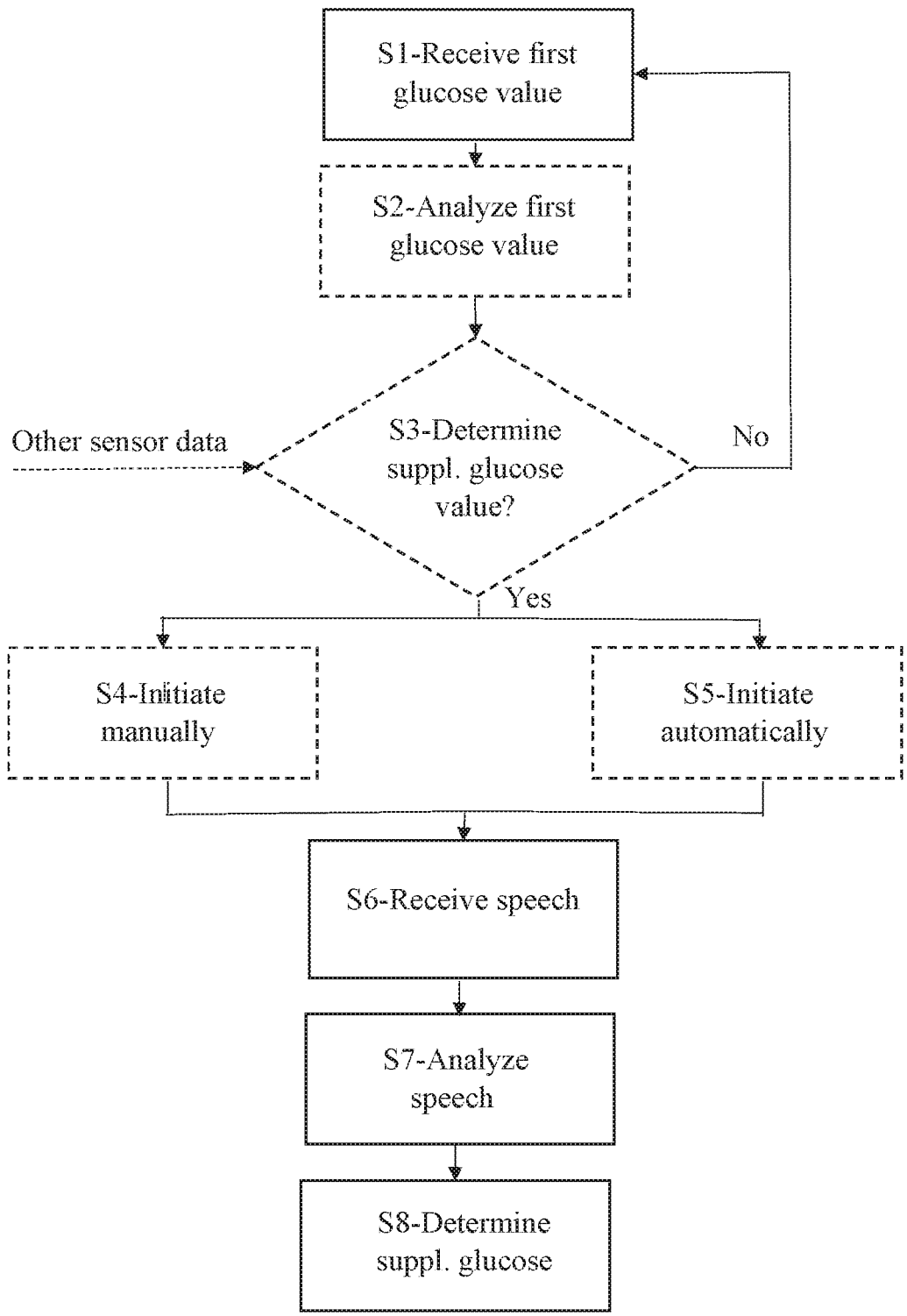
FIG. 3 is a flow diagram illustrating an embodiment of a method for monitoring a blood glucose level.

FIG. 3 is a flow diagram illustrating a method that can be performed in a glucose monitor 10 as described above or any other device or system which is suitable for performing the method. The following disclosure will refer to an implementation in the glucose monitor 10 shown in FIG. 2.

The method comprises the main steps of receiving, step S1, a first glucose value, which has been measured in a body fluid of the individual other than the individual's blood, the first glucose value representing the blood glucose level of the individual with a first delay; receiving, step S6, speech of the individual; analyzing, step S7, the individual's speech; and determining, step S8, a supplementary glucose value, which represents the blood glucose level of the individual with a shorter delay than the first delay; wherein the determination of the supplementary glucose value is based on the analyzing of the individual's speech.

In some embodiments, steps S6-S8 of receiving speech, analyzing the individual's speech and determining the supplementary glucose value are selectively initiated.

The selective initiation of steps S6-S8 of receiving speech, analyzing the individual's speech and determining the supplementary glucose value may be based on different data.

Some embodiments comprise the step S2 of analyzing the first glucose value and selectively initiating steps S6-S8 of receiving speech, analyzing the individual's speech and determining the supplementary glucose value based on the result of the analyzing of the first glucose value.

In some embodiments, steps S6-S8 of receiving speech, analyzing the individual's speech and determining the supplementary glucose value are selectively initiated depending on a detected physical activity of the individual.

More particularly, in the first step S1, the first glucose value is received from the glucose sensor 11 on the first interface 13 of the glucose monitor 10. It may be presented to the user directly on the user output interface 17.

The first glucose value is analyzed by the control circuitry 15 in optional step S2. The analysis may comprise different kinds of calculations performed on the received glucose value or on a set of received glucose values. Examples of such calculations include averaging, calculations of trends, comparison with one or more predefined threshold values or intervals and conversion to other scales or other units. The calculations may also involve use of more sophisticated algorithms. The analysis may furthermore take other parameters than the first glucose value(s) into account. Such parameters may include information about the diabetic's sleep, food intake and physical activities and may be received from sensors recording these parameters, such as the other sensor 19, or from user input on the user input interface 16.

One purpose of the calculations may be to provide a result that can be presented to the diabetic in a suitable form on the user output interface 17. Another purpose may be to assess whether the glucose value is moving away from a normal range. Yet another purpose may be to obtain a result on the basis of which it can be assessed whether a supplementary glucose value need to be determined.

In optional step S3, it is decided, by the control circuitry 15, whether a supplementary glucose value should be determined. The decision may be based on the result of the analysis in step S2. However, it may alternatively or as a complement be based on other input, e.g. data from the other sensor 19 of the glucose monitor 10. The sensor 19 may for instance measure a parameter that reveal that the diabetic is physically active. For that purpose, the sensor 19 may comprise a pulse sensor which measures the diabetic's pulse and/or an accelerator and/or a GPS that measures the diabetic's movements. Since physical activity may affect the blood glucose level, it may be desirable to check the development of the blood glucose level by means of the supplementary glucose value if prolonged or intense physical activity is detected. Other detected physical conditions of the diabetic, like his body temperature or sleep patterns, may also be used as an input or trigger to decide whether a supplementary glucose value should be determined.

If the answer to the question in step S3 is no, the flow returns to step S1 and the receipt of the next first glucose value. If the answer is yes, the determination of the supplementary glucose value is initiated. The initiation may be manual, optional step S4, or automatic, optional step S5.

In some embodiments, steps S6-S8 of receiving speech, analyzing the individual's speech and determining the supplementary glucose value are automatically initiated.

The automatic initiation includes one or more steps carried out by the control circuitry 15 of glucose monitor 10 without assistance of the diabetic or any other user. These steps may include turning on the microphone, prompting the diabetic to start speaking, and starting the recording of the speech from the diabetic.

Some embodiments comprises creating, on the basis of the analyzing of the first glucose value, a prompt to the individual to manually initiate, step S4, the steps of receiving speech, analyzing the individual's speech and determining the supplementary glucose value.

The prompt, which may be output on the user output interface 17, may alternatively or additionally be sent to another user of the system, e.g. a parent who monitors a diabetic child, via a user communication device 22.

The manual initiation requires an action from the diabetic or another user, such as pressing a button, inputting a voice command, or providing any other kind of input to the user input interface 16 of the glucose monitor 10 to confirm that a supplementary glucose value should be determined based on a recording of the individual's speech.

Steps S6-S8 may also be manually initiated without any prompt from the system. The diabetic may for instance feel that his condition does not correspond to the glucose values measured by the glucose sensor 11 and presented to him on the user output interface 17 and choose to manually initiate the speech recording and speech analysis to check if the supplementary glucose value better corresponds to what he feels.

One or more of the optional steps S2-S5 above are carried out in order to selectively trigger the determination of the supplementary glucose value. However, in some other embodiments, the determination of the supplementary glucose value is not selectively triggered, but is performed in parallel to the measurement of the first glucose value in the body fluid. The determination may be carried out continuously or during predetermined periods so that no selective triggering is needed. It may be an advantage to always have two differently established glucose values available, one which represents the blood glucose level with some delay, and one which represents the blood glucose level in real-time or near real time, to assess the development of the blood glucose value. However, continuously recording and analyzing the speech of the diabetic, may require a lot of power and may thus drain any battery of the glucose monitor 10.

In some embodiments, the first glucose value is measured at a first point in time and the steps of receiving speech, analyzing the individual's speech and determining the supplementary glucose value are performed within a predetermined time of the first point in time.

The first point in time may be the time at which the first glucose value is received by the glucose monitor 10, a time when the analysis of the first glucose value establishes that the first glucose value deviates from the normal, a time when the diabetic indicates that he or she has taken an action to correct the blood glucose level, or the like. The determining of the supplementary glucose value may be set to be automatically initiated by the control circuitry 15 within a predetermined time of the first point in time in order to ensure that any deviation has been fixed or any corrective action has resulted in a desired blood glucose level.

In step S6, speech from the individual is received via microphone 12 on the interface 14.

In step S7, the individual's speech is analyzed by the control circuitry 15. The analysis of the speech may be carried out in a number of ways, but basically it is based on a comparison of characteristics or features of the received speech on the one hand, with characteristics or features of speech that has been recorded under stable and normal glucose conditions, on the other hand, and a calibration of the changes in these characteristics or features to changes in blood glucose level. Examples of useful characteristics or features include frequency patterns and amplitude patterns in the speech spectrum. U.S. Pat. No. 7,925,508 and WO 2014/049438 include examples of how speech may be analyzed and calibrated to blood glucose levels.

In step S8, the supplementary glucose value is determined by the control circuitry 15 based on the analyzing of the individual's speech. It may be presented to the diabetic on the user output interface 17 and/or to any other user of the system, e.g. via the user communication device 22.

Figure 4:
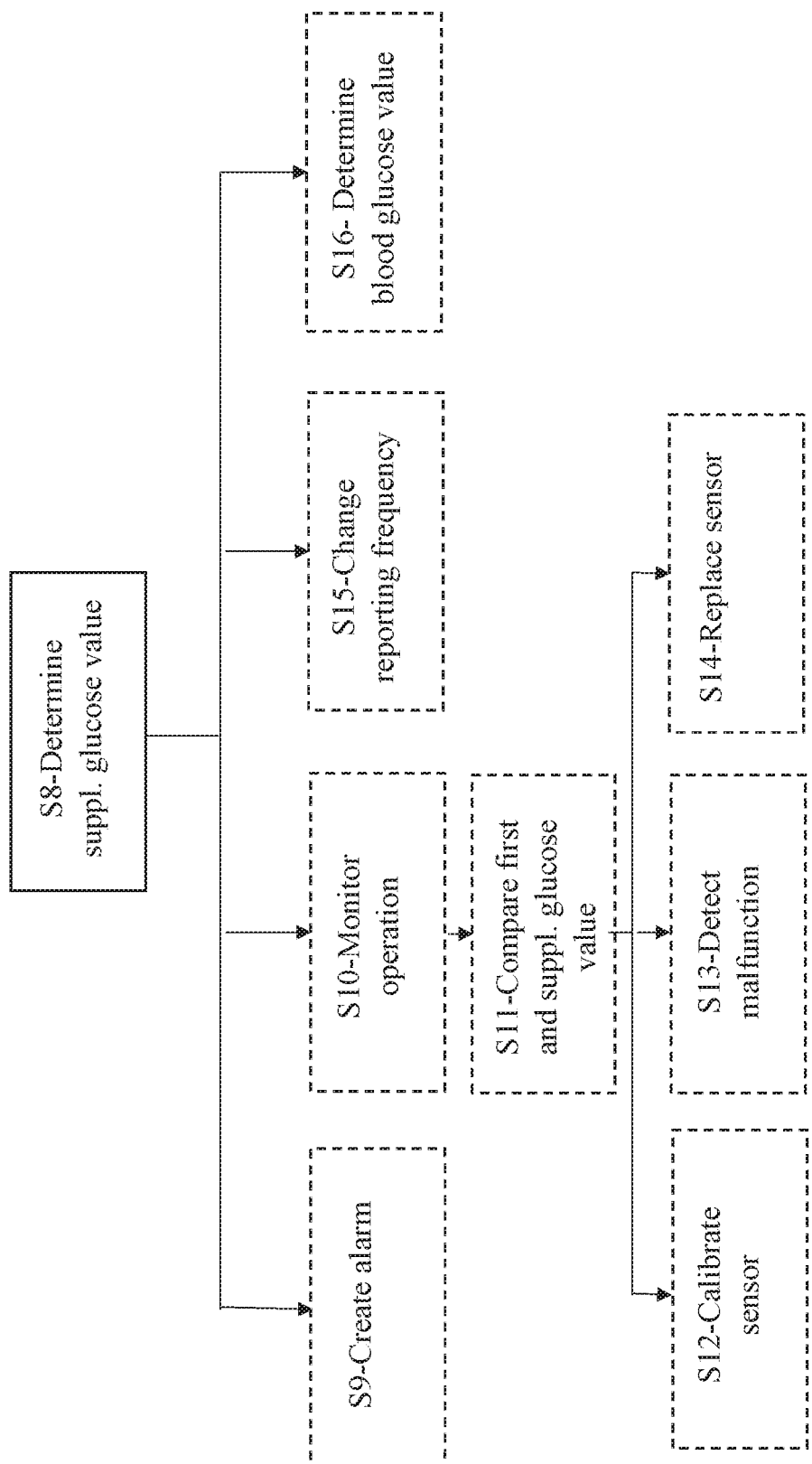
FIG. 4 is a flow diagram illustrating different optional steps that could be included in some embodiments of a method for monitoring a blood glucose level.

The supplementary glucose value may also be used for further operations as will be explained in the following with reference to FIG. 4.

In some embodiments, the method comprises the optional step S9 of creating an alarm, when the supplementary glucose value indicates that the blood glucose level is below a first predetermine threshold value or above a second predetermined threshold value. The alarm may be presented to the diabetic on the output user interface 17.

The first predetermined threshold value may correspond to a limit below which the blood glucose level is judged to be too low and the second predetermined threshold value may correspond to a limit above which the blood glucose level is judged to be too high. In some embodiments, the glucose monitor 10 may store a series of different predefined thresholds, enabling the creation of different alarms depending on how serious the condition of the diabetic is judged to be. Different alarms may also be sent to different users at different times, e.g. a first alarm to the diabetic and a second alarm to another user of the system if the glucose monitor 10 detects that no corrective action is taken within a predetermined time.

In some embodiments, the method comprises the optional step S10 of monitoring the operation of a sensor used for measuring the first glucose value on the basis of the supplementary glucose value.

More particularly the glucose sensor 11 may be monitored continuously or intermittently in periods. The monitoring may be triggered automatically by the glucose monitor 10 or manually by the diabetic or another user.

In some embodiments, optional step S11 comprises comparing the first glucose value and the supplementary glucose value taking a difference between the first delay and the shorter delay into account.

The comparison may involve one or more first glucose values and one or more supplementary glucose values. A sequence of supplementary glucose values determined from the individual's speech may for instance be mapped to a sequence of glucose values from the glucose sensor, taking the different delays into account.

In some embodiments the method comprises the optional step S12 of using a result of the comparing step for calibrating the sensor used for measuring the first glucose value.

The glucose sensor 11 may have a sensor head that is placed in the body fluid in which the glucose level is to be measured. Due to clogging, tear or wear, change of position, use of drugs, skin irritations or the like, the glucose sensor 11 may need to be calibrated during use. The need for calibration may be detected by comparing how the relation between the first glucose values and the supplementary glucose values changes over time, or between a first point in time and a second point in time. The supplementary glucose value may then be used to calibrate the glucose sensor 11, or a blood sample may be taken, analyzed and then used for calibrating the sensor 11.

In some embodiments, the method comprises the optional step S13 of using a result of the comparing step for detecting malfunction of the sensor used for measuring the first glucose value.

A comparison between the first glucose value and the supplementary glucose value may reveal that the glucose sensor 11 is broken or out of order. A sudden change in the relation between the first glucose value and the supplementary glucose value may be one sign of this. If a malfunction is detected, the speech-based glucose measurement may be used as a back-up until the glucose sensor 11 has been fixed or replaced.

In some embodiments, the method comprises the optional step S14 of using a result of the comparing step for determining when the sensor used for measuring the first glucose value is to be replaced.

As is well-known, glucose sensors that are carried on the body need to be replaced with a certain periodicity. Today a diabetic is instructed to change a CGM sensor within a standardized period of typically 14 days. By using the result of the comparison between the first glucose value and the supplementary glucose value, an individual assessment can be done to ascertain when the glucose sensor 11 need to be replaced. This may result in both shorter and longer periods between the change. Detecting that a sensor need to be replaced before the standard point in time may result in a higher and more even quality in the glucose measurement. Detecting that a sensor need to be replaced later than the standard point in time may result in cost savings.

In some embodiments the method comprises the optional step S15 of reporting the first glucose value to a user at a first frequency when the supplementary glucose value indicates that the blood glucose level is within a first range and reporting the first glucose value to a user at a second frequency when the supplementary glucose value indicates that the blood glucose level is within a second range.

A first reporting frequency may be used when the first glucose value indicates a normal blood glucose level, and a second reporting frequency, which is higher than the first one, may be used when the first glucose value indicates that the blood glucose value deviates from the normal so that the diabetic and/or any other user of the system can follow the development more closely when the first glucose value indicates an undesired condition.

In some embodiments, the method comprises the optional step S16 of determining a current blood glucose level on the basis of both the first glucose value and the supplementary glucose value. The current blood glucose level may be determined based on a weighted combination of the first glucose value and the supplementary glucose value.

Even if the supplementary glucose value represents the blood glucose value with no or little lag, the supplementary glucose value may not be as exact as the glucose value measured by the glucose sensor 11. In some situations a better indication may therefore be provided by combining the first glucose value measured by the glucose sensor 11 with the supplementary glucose value. The different values may be combined in different ways to form the current blood glucose value. Examples of different combinations include linear or non-linear combinations with different weights on the different values.

As mentioned above, the glucose sensor 11 needs to be changed periodically. It may however take some time after a change until the operation of the glucose sensor 11 is stable. Until such time, speech-based glucose analysis may be used as a back-up and/or complement. Immediately after the change, the glucose value indicated to the diabetic, may be entirely based on the supplementary glucose value. As time passes and the operation of the glucose sensor stabilizes, the glucose value indicated to the diabetic may be based on a combination of the two different glucose values, where successively more weight is put on the glucose value from the glucose sensor 11 until its operation is deemed to have been full stabilized.

All the steps S9-S16 may be implemented by the control circuitry 15 of the glucose monitor 10.

Figure 5:
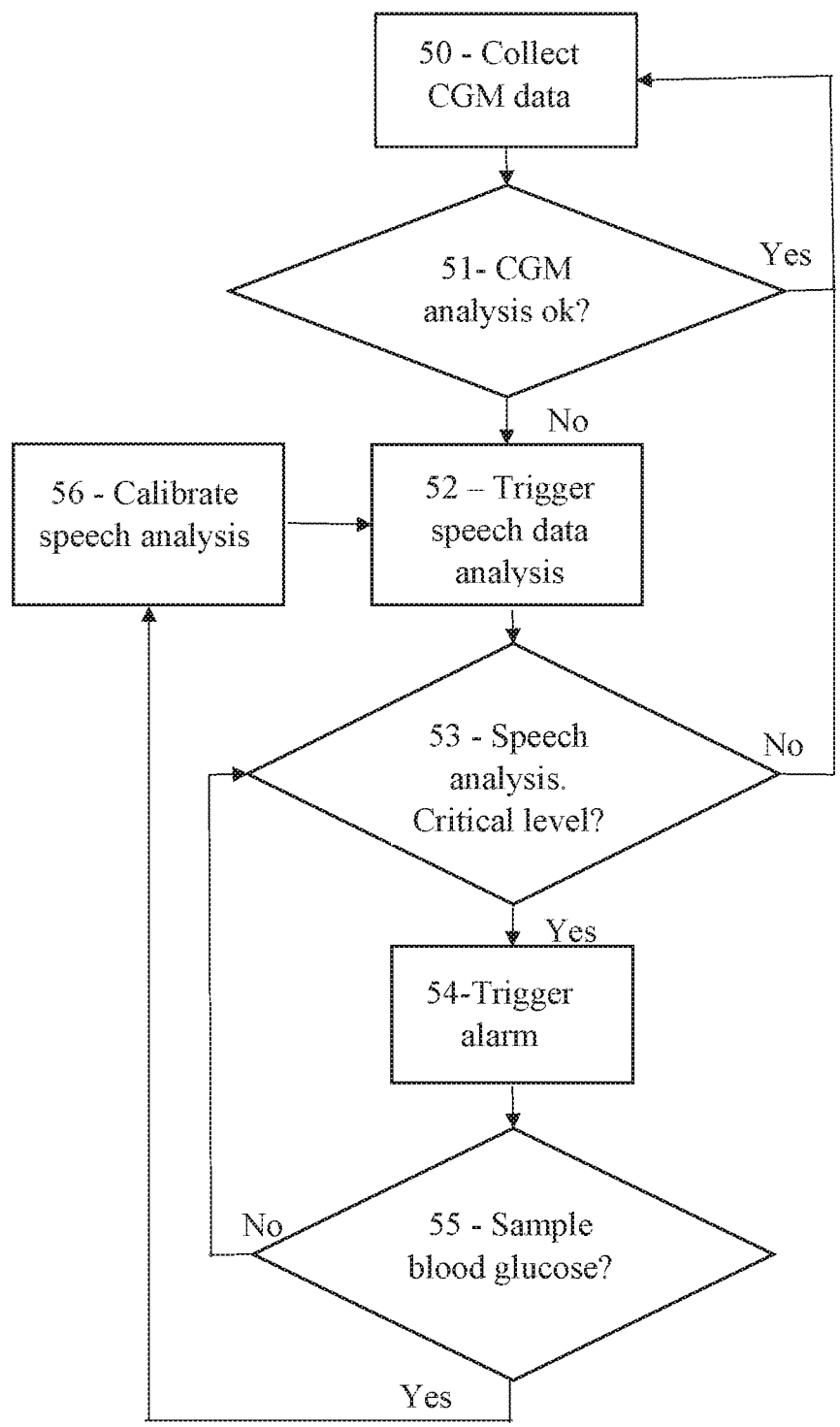
FIG. 5 is a flow diagram illustrating another embodiment of a method for monitoring a blood glucose level.

FIG. 5 is a flow diagram illustrating an embodiment of the method, which may be implemented in a glucose monitor 10 as described above. In step 50, glucose data is collected from a CGM sensor, i.e. a sensor for Continuous Glucose Measurement. In a next step 51, the CGM data is analyzed and checked to see if the glucose level is acceptable. If so is the case, steps 50 and 51 are repeated. If the analysis indicates that the glucose level is not ok (e.g. absolute level out of normal range or level indicating an unacceptable trend), collection of speech data is triggered in step 52. In subsequent step 53, the speech data is analyzed and checked to see if the speech data confirms that the glucose level is at a critical level. If not, the speech data collection is interrupted and steps 50 and 51 are repeated again. If the speech data confirms the findings of the CGM analysis, an alarm is triggered in step 54. In the following step 55, the user is prompted to sample the blood glucose level by taking a blood sample and analyzing it in a traditional glucose meter. If no blood glucose level sample is taken, the flow returns to step 53 and the speech analysis continues to check if the glucose level improves. If a blood sample is taken and a current blood glucose level is obtained, it is used in step 56 to calibrate the speech analysis, and then the speech data collection is again triggered in step 52. According to this embodiment, the supplementary glucose value is used as a complement to the CGM to confirm and/or reject the findings of the CGM analysis, and as an intermediary step, before confirmation by ordinary blood sample is required. In this way, the diabetic may avoid taking a number of blood samples. Also, in situations where a blood sample analysis is not available, the speech-based supplementary glucose value will serve as a real-time indication of the blood glucose level.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A method for monitoring a blood glucose level of an individual, comprising the steps of
receiving a first glucose value, which has been measured in a body fluid of the individual other than the individual's blood, the first glucose value representing the blood glucose level of the individual with a first delay;
analyzing the first glucose value to determine whether the represented blood glucose level is acceptable; and
when the represented blood glucose level is determined to be unacceptable, initiating the steps of:
receiving speech of the individual;
analyzing the individual's speech; and
determining a supplementary glucose value, which represents the blood glucose level of the individual with a shorter delay than the first delay; wherein the determination of the supplementary glucose value is based on the analyzing of the individual's speech.

2. The method of claim 1, wherein the steps of receiving speech, analyzing the individual's speech and determining the supplementary glucose value are selectively initiated depending on a detected physical activity of the individual.

3. The method of claim 1, wherein the steps of receiving speech, analyzing the individual's speech and determining the supplementary glucose value are automatically initiated.

4. The method of claim 1, further comprising creating a prompt to the individual to manually initiate the steps of receiving speech, analyzing the individual's speech and determining the supplementary glucose value.

5. The method of claim 1, wherein the first glucose value is measured at a first point in time and wherein the steps of receiving speech, analyzing the individual's speech and determining the supplementary glucose value are performed within a predetermined time of the first point in time.

6. The method of claim 1, further comprising the step of creating an alarm, when the supplementary glucose value indicates that the blood glucose level is below a first predetermined threshold value or above a second predetermined threshold value.

7. The method of claim 1, comprising the step of reporting the first glucose value to a user at a first frequency when the supplementary glucose value indicates that the blood glucose level is within a first range and reporting the first glucose value to a user at a second frequency when the supplementary glucose value indicates that the blood glucose level is within a second range.

8. The method of claim 1 further comprising the step of determining a current blood glucose level on the basis of both the first glucose value and the supplementary glucose value.

9. The method of claim 8, wherein the current blood glucose level is based on a weighted combination of the first glucose value and the at least one supplementary glucose value.

10. The method of claim 1, further comprising the step of monitoring the operation of a sensor used for measuring the first glucose value on the basis of the supplementary glucose value.

11. The method of claim 10, wherein the monitoring comprises the step of comparing the first glucose value and the supplementary glucose value taking a difference between the first delay and the shorter delay into account.

12. The method of claim 11, further comprising the step of using a result of the comparing step for calibrating the sensor used for measuring the first glucose value.

13. The method of claim 11, further comprising the step of using a result of the comparing step for detecting malfunction of the sensor used for measuring the first glucose value.

14. The method of claim 11, further comprising the step of using a result of the comparing step for determining when the sensor used for measuring the first glucose value is to be replaced.

15. A device for monitoring a blood glucose level of an individual, comprising a first interface for receiving a first glucose value, which has been measured in a body fluid of the individual other than blood, the first glucose value representing the blood glucose level of the individual with a first delay, a second interface for receiving speech from the individual; and control circuitry configured to: analyze the first glucose value to determine whether the represented blood glucose level is acceptable; determine, when the representative blood glucose level is determined to be unacceptable, that a supplementary glucose value needs to be determined; analyze the individual's speech; and determine at least one supplementary glucose value, which represents the blood glucose level of the individual with a shorter delay than the first delay; wherein the determination of the at least one supplementary glucose value is based on the analyzing of the individual's speech.

16. The device of claim 15, wherein the device is a wearable configured to be carried by the individual.

17. The device of claim 15, wherein the device is enabled for connection to a computer network.

18. A system comprising a device for monitoring a blood glucose level of an individual, comprising a first interface for receiving a first glucose value; which has been measured in a body fluid of the individual other than blood, the first glucose value representing the blood glucose level of the individual with a first delay, a second interface for receiving speech from the individual, and control circuitry configured to; analyze the first glucose value to determine whether the represented blood glucose level is acceptable; determine, when the represented blood glucose level is determined to be unacceptable, that a supplementary glucose value need to be determined; analyze the individual's speech; and determine at least one supplementary glucose value, which represents the blood glucose level of the individual with a shorter delay than the first delay; wherein the determination of the at least one supplementary glucose value is based on the analyzing of the individual's speech; and a sensor for measurement of the first glucose value.

* * * * *